United States Patent [19]

Jennings et al.

[11] 4,265,860
[45] May 5, 1981

[54] HIGH PRESSURE SOXHLET EXTRACTOR

[75] Inventors: Walter G. Jennings, Davis; Robert H. Wohleb, Orangevale; Norman W. Wohlers, Davis, all of Calif.

[73] Assignee: J & W Scientific, Incorporated, Rancho Cordova, Calif.

[21] Appl. No.: 134,625

[22] Filed: Mar. 27, 1980

[51] Int. Cl.³ ............................................ B01D 11/02
[52] U.S. Cl. .................................. 422/280; 202/169; 422/101
[58] Field of Search .............. 422/101, 280, 281, 285, 422/288, 290; 202/168, 169, 170, 170 D; 156/DIG. 90

[56] References Cited

U.S. PATENT DOCUMENTS

| 2,006,513 | 7/1935 | Rascher et al. | 422/101 |
| 2,095,056 | 10/1937 | Clough | 202/168 X |
| 2,478,619 | 8/1949 | Arnold | 422/101 X |
| 3,107,205 | 10/1963 | Moran et al. | 422/101 X |
| 4,006,062 | 2/1977 | Bhuchar et al. | 422/101 X |

FOREIGN PATENT DOCUMENTS

| 844363 | 9/1952 | Fed. Rep. of Germany | 202/168 |
| 547772 | 9/1942 | United Kingdom | 422/280 |

Primary Examiner—Joseph Scovronek
Attorney, Agent, or Firm—Lothrop & West

[57] ABSTRACT

The numerous advantages of a Soxhlet apparatus are combined with the nice pressure and temperature controls afforded by a pressure vessel to enlarge the scope and efficacy of both pieces of equipment. A judicious selection of solvent, such as $CO_2$, provides a solvent-free extract which is ideal for gas chromatographic studies and can advantageously be used in an ever-widening spectrum of analyses including research, food and flavor, pheromone analysis and essence extraction. The extraction of oil from coal and oil shale, in comminuted form, is also facilitated by the use of the apparatus operated under reflux conditions, controlled pressure-temperature relations and appropriate choice of extractant.

6 Claims, 1 Drawing Figure

U.S. Patent
May 5, 1981
4,265,860
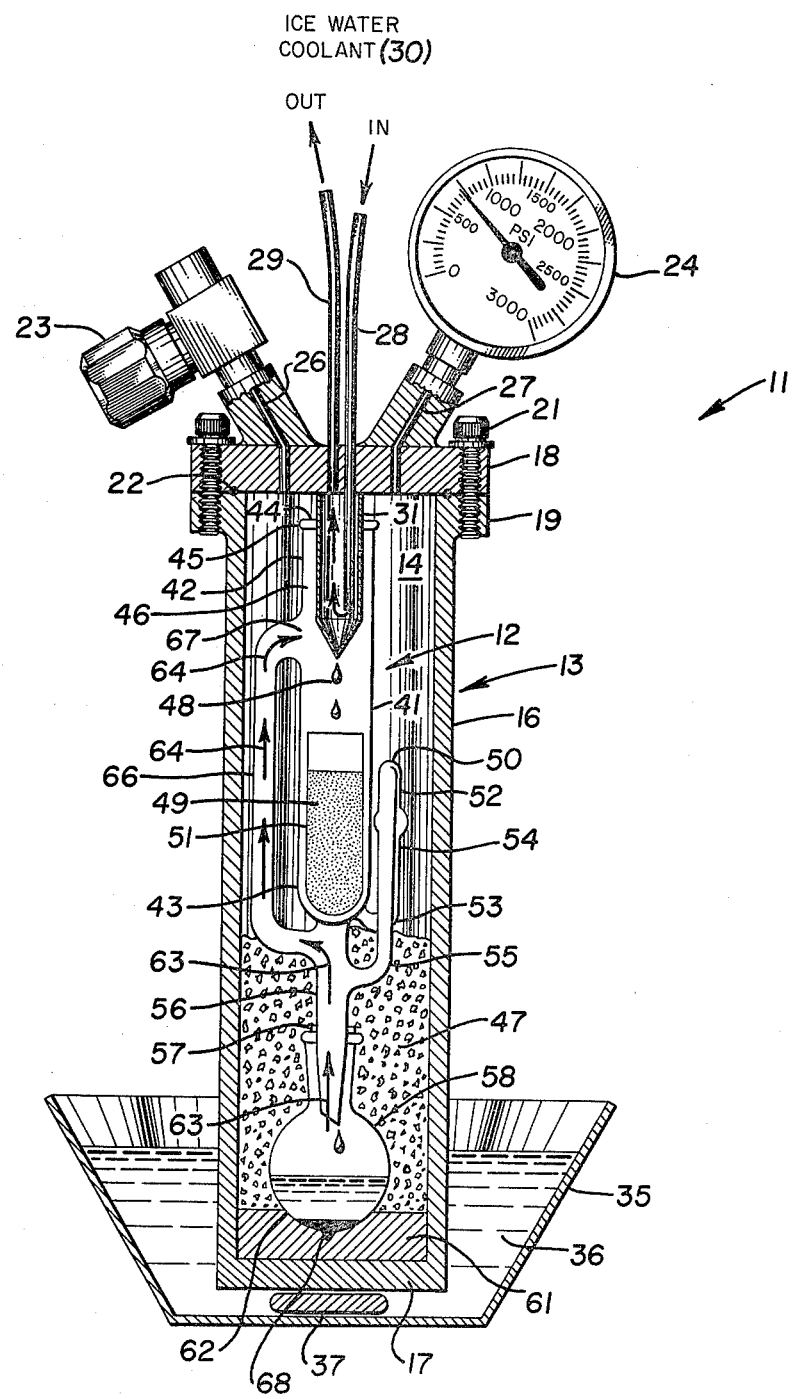

HIGH PRESSURE SOXHLET EXTRACTOR

CROSS-REFERENCE TO RELATED APPLICATIONS

United States Design Patent Application, Ser. No. 929,452, Filed July 31, 1978.

BACKGROUND OF THE INVENTION

The principle of Soxhlet extraction is not new.

Invented by Franz von Soxhlet, a German agricultural chemist who died in 1926, Soxhlet apparatus has long been used in extracting fatty or other material with a volatile solvent (e.g. ethyl ether, alcohol or benzene).

A Soxhlet apparatus comprises a vertical glass cylindrical extraction tube that has both a siphon tube and a vapor tube, that is fitted at its upper end to a reflux condenser and at its lower end to a flask so that the solvent may be distilled from the flask into the condenser. From the condenser the solvent in liquid phase flows back into the cylindrical tube which holds the sample to be extracted in a porous thimble. When the solvent level rises to the top of the siphon tube the solvent, with the extracted materials, is siphoned over into the flask, to be distilled again, and thus start another cycle.

Other solvents, such as carbon disulfide, pentane, and Freon have also been used in Soxhlet extraction.

After a sufficient period of time, all extractable matter in the sample is located in the flask, along with a major portion of the solvent, which is usually removed by evaporation. Depending on the amount of solvent and its boiling point, evaporation as a process for removing the solvent can result in appreciable losses of volatile constituents of the sample.

Fixed gases, such as carbon dioxide, can also be obtained as liquids at a suitably elevated pressure. Carbon dioxide, being molecularly similar to carbon disulfide, is also an excellent extractant. Owing to its low boiling point ($-80°$ C.) it can be removed at low temperature without the loss of volatile sample constituents.

Carbon dioxide has in fact been previously utilized as an extractant (see, for example, Schultz et al, Pilot-Plant Extraction With Liquid $CO_2$, 32 Food Technology, June 1974) but in most instances has required the fabrication of highly specialized and expensive apparatus.

There is, in other words, considerable room for improvement.

SUMMARY OF THE INVENTION

The present invention permits the use of standard glass extractors, such as a Soxhlet apparatus, by housing the entire assembly in a pressure vessel, thereby equalizing pressures inside and outside the extractor and the flask.

The operation is facilitated by the use of a heat transfer plate associated with the pressure vessel and a magnetic stirrer to agitate the heated water bath.

The result is a solvent-free extract that is ideal for gas chromatographic studies. The high pressure extractor of the present invention is also ideal for sensory or organoleptic evaluation, or for the isolation of pheremones or insect attractants, and is to be advantageously contrasted with conventional techniques which produce extracts having residual solvents seriously complicating the interpretation of response.

Extracts prepared in accordance with the pressure system of the present teachings are solvent free, thereby permitting responses to be interpreted as being due to the extract and not to residual solvent.

Although the following specifications call, for the most part, for the use of carbon dioxide as the extractant, it is especially to be noted that our apparatus and method are not limited thereto.

A listing of all of the various solvents capable of being used with the high pressure extractor of the present invention would span several hundred compounds, some of which are relatively obscure but which may possess peculiar or unique solvent properties that could make them superior for very specific extractions that may not yet be envisioned.

It can be said, however, that the present apparatus can effectively utilize, as a solvent, any material whose critical temperature (i.e. gas conversion temperature) falls in the range of $-30°$ C. to $+200°$ C. at pressures of one to 200 atmospheres.

The most critical property for many applications is the extraction properties of the condensed liquid, in which case the pressure and temperature parameters are appropriately adjusted to suit the extractant selected as a result of its extraction characteristics.

In some cases, $CO_2$ is ideal, the extraction properties being about the same as ethyl ether, (according to Schultz et al, supra) with a low boiling point to facilitate solvent removal and being easily condensable to facilitate solvent recovery.

For other applications, one of the Freons, e.g. Freon 12 (dichlorodifluoro methane), might be superior; and, in some instances, ammonia might have better solubility characteristics.

In most cases, the solubility properties of a solvent are of major interest. However, it is sometimes the solvent's ability to discourage the adsorption of solute on a substrate (i.e. a high heat of adsorption); and sometimes it is the temperature-vapor pressure relationship of the solvent that is of especial concern. These factors must all be balanced for a particular application.

Of not inconsiderable interest is the fact that $CO_2$ proves to be a good solvent in the extraction of some oils from coal as well as from oil shale.

BRIEF DESCRIPTION OF THE DRAWING FIGURE

The FIGURE is a median vertical sectional view of the pressure vessel with enclosed Soxhlet apparatus and flask, the heated water bath and magnetic stirrer being shown in schematic fashion.

DETAILED DESCRIPTION OF A PREFERRED EMBODIMENT

While the high pressure Soxhlet extractor of the invention is susceptible of numerous physical embodiments, depending upon the environment and requirements of use, substantial numbers of the herein shown and described embodiment have been made, tested and used, and have performed in an eminently satisfactory manner.

The extractor of the invention, generally designated by the reference numeral 11, broadly comprises two major components, a glass Soxhlet extractor 12 and a pressure vessel 13 affording a vertically elongated chamber 14 housing the extractor during operation of the unit.

The pressure vessel 13 includes a hollow, vertically-elongated, right circular cylinder 16 enclosed at the bottom by a circular disc 17 and at the top by a circular removable cap 18, or cover.

The upper end of the cylinder 16 is enlarged by the addition of an annular flange 19 to provide a conjugate surface in engagement with the superposed cover 18. Strong (such as grade "8") stainless steel machine screws 21 removably secures the cap 18 and an O-ring 22 affords a good seal.

The circular cover 18 provides a convenient base for a high pressure (e.g. 3000 psi) stainless steel needle valve fitting 23 and a correspondingly high pressure stainless steel pressure gauge 24.

In addition to the passageways 26 and 27, respectively, extending through the needle valve fitting 23 and the pressure gauge 24, two conduits 28 and 29 are provided. The conduit 28 serves to conduct ice water coolant 30, into a finger type condenser 31 and the conduit 29 leads the ice water 30 out of the condenser 31.

The lower end of the cylinder 16 is submerged in a container 35 providing a heated water bath 36 during operation of the invention, the body of water 36 being heated by any suitable means (not shown) and agitated by appropriate mixing devices, such as a magnetic stirrer 37.

The Soxhlet extractor 12 is vertically disposed within the chamber 14 and includes, in known fashion, a vertically disposed cylindrical tube 41, or extractor body, extending from an upper end 42 to a lower end 43.

The upper end 42 of the body tube 41 is formed with an opening 44 to permit the placement of the condenser 31 therein. Since the diameter of the opening 44 exceeds the diameter of the condenser 31 an annular passageway 46 is provided for the downward flow of $CO_2$ vapor sublimating from a body 47 of comminuted $CO_2$ in solid state ("dry ice"). The $CO_2$ vapor ascends to the upper end of the tube 41 then curves over the upper lip 45 to descend through the annular passageway 46.

As the $CO_2$ in vapor phase flows downwardly through the annular passageway 46 and alongside the chill outer walls of the condenser 31, the $CO_2$ vapor is condensed and descends in liquid form, as indicated by the droplets 48.

The liquid $CO_2$ falls onto the sample 49 of extractable material, including preloaded porous polymers, activated charcoal or the like, located in an extraction thimble 51 disposed in the lower end portion of the extractor tube 41. The extraction properties of the liquid $CO_2$ then take effect and when the level of the liquid solvent plus the extracted material reach the top 50 of a siphon tube 52 having its lower end 53 in communication with the lower end 43 of the extractor body 41, the solvent plus the extracted material are siphoned upwardly out of the first leg 54, over the top 50 thence downwardly through the second leg 55 and into a vertical glass conduit 56 leading through a stopper 57 into a flask 58, or vial.

The flask 58 is heated, an aluminum heat transfer plate 61 providing a very satisfactory thermal mass. Heat flows from the water bath 36, which is heated in any desired manner, as by hot plate or burner, not shown, through the bottom 17 and into the heat transfer plate 61. The magnetic stirrer 37 serves to augment the natural convection currents in the bath 36 and thus helps to maintain uniformity of temperature throughout the bath.

Preferably a depression 62 is formed in the top of the heat transfer plate 61 to receive the bottom of the flask 58, the heat from the plate 61 passing into the flask and distilling the liquid $CO_2$ while allowing the extracted material to collect.

In other words, the liquid $CO_2$ in the flask is turned to vapor and rises through the conduit 56, as indicated by the arrows 63 while the extracted material remains in the vial.

It is believed appropriate, at this juncture, to note that during customary operation the interior of the pressure vessel 13 is at a substantially elevated pressure, namely, 600–700 psi. Thus, the liquid $CO_2$ can be distilled into vapor phase at a temperature which is low enough as not to cause the loss of volatile sample constituents, yet allowing the $CO_2$ vapor to be readily condensed by the finger condenser 31. As indicated by the arrows 64 the $CO_2$ vapor ascends from the conduit 56, through the side arm vapor tube 66 and emerges from the opening 67 into impingement with the condenser 31. The $CO_2$ vapor thereupon turns to liquid and descends as droplets 48, merging with the droplets 48 previously described as being derived from the sublimated vapor from the body of dry ice 47.

As the combined droplets 48 descend into the sample 49, the distillation-condensation cycle is complete and a new cycle is ready to begin.

Several hours of the cycling operation may be required for full extraction. If the unit is placed in a shallow pan of dry ice immediately following extraction, the pressure soon drops to a very low level. The needle valve 23 can then be opened and the cover 18 removed. At room temperature and pressure, the $CO_2$ vaporizes into the atmosphere leaving the extracted material in the flask 58. The flask is then separated from the Soxhlet unit and the extracted material 68 is recovered with a syringe, by vacuum transfer or by rinsing the flask 58 with a minimum amount of an appropriate solvent.

Where $CO_2$ is used as the extractant, the process is particularly convenient and easy, it being merely necessary to add the appropriate quantity of dry ice and secure the cover so as to close the assembly. As the dry ice vaporizes, the pressure will rise to about 850 to 1000 psi. The ice water coolant 30 is then passed through the cold finger condenser 31 as previously described. As condensation begins, the pressure will fall to a reading on the gauge 24 of about 600–700 psi. At these pressures, any water or other impurities introduced with the dry ice will remain outside the extraction assembly while only pure $CO_2$ condenses and is delivered to the Soxhlet apparatus for cycling in accordance with the reflux conditions heretofore disclosed.

As has been noted, $CO_2$ has extraction properties similar to those of ethyl ether, and if water is present in the sample 49, the water will be extracted together with the other constituents. On some occasions an oil can be recovered from the water layer, or a small quantity of dichloromethane can be used to separate and recover the non-aqueous constituents. Five to ten $\mu l$ of dichloromethane can beneficially be added to the sample prior to commencement of the extraction process to serve as a carrier. Alternatively, excellent chromatographic results can be obtained by direct aqueous injection of these solutions on glass capillary columns.

It can therefore be seen that the high pressure extractor of our invention makes it easy to take advantage of the excellent solvent properties of liquid $CO_2$, provides a low temperature, inert atmosphere which minimizes artifact formation, readily desorbs volatiles from porous polymer traps or activated charcoal substrates, allows recovery of low boiling compounds, yields essentially complete recovery of compounds in a solvent-free system and finds applications in a wide variety of analyses including research, food and flavor analysis, essence extraction and pheremone analysis.

We claim:

1. A high pressure Soxhlet extractor comprising:
   a. a Soxhlet apparatus including an extractor body, a flask and a condenser;
   b. a pressure vessel encompassing said Soxhlet apparatus, said vessel comprising a vertically elongated hollow cylinder having a bottom cover and a removable top cover;
   c. means for heating said pressure vessel to distil an extractant in said flask;
   d. means for chilling said condenser to liquefy the distilled extractant;
   e. a thimble containing a sample having soluble constituents disposed in said extractor body below said condenser to receive the extractant in liquid phase descending by gravity from said condenser; and,
   f. siphon means for periodically carrying the extractant and sample constituents from said extractor body to said flask to resume cycling of the extractant while collecting the extracted material.

2. An extractor as in claim 1 including conduit means connecting said flask and said extractor body for carrying the extractant in vapor phase from said flask into said extractor body in the vicinity of said condenser for liquefaction thereby.

3. An extractor as in claim 2 further including a heat transfer plate located on said bottom cover and interposed between said bottom cover and said flask; and in which said heating means comprises a heated water bath having the lower end of said cylinder immersed therein.

4. An extractor as in claim 3 in which said chilling means includes a pair of tubes leading from said condenser through said top cover, one of said tubes carrying a stream of water toward said condenser and the other of said tubes carrying the stream of water away from said condenser after said condenser is cooled thereby.

5. An extractor as in claim 4 including a needle valve fitting on said top cover, said fitting being in communication with the interior of said cylinder in order selectively to vent the pressure in said cylinder; and a pressure gauge on said top cover in operative communication with the interior of said cylinder.

6. An extractor as in claim 5 in which $CO_2$ is the extractant and in which dry ice deposited in the lower portion of said cylinder is the source of the $CO_2$.

* * * * *